US00PP28471P3

(12) United States Plant Patent
Layt

(10) Patent No.: US PP28,471 P3
(45) Date of Patent: Oct. 3, 2017

(54) ***RHAGODIA SPINESCENS* PLANT NAMED SAB01**

(50) Latin Name: *Rhagodia spinescens*
Varietal Denomination: SAB01

(71) Applicant: Todd Anthony Layt, Clarendon (AU)

(72) Inventor: Todd Anthony Layt, Clarendon (AU)

( * ) Notice: Subject to any disclaimer, the term of this patent is extended or adjusted under 35 U.S.C. 154(b) by 49 days.

(21) Appl. No.: 14/756,671

(22) Filed: Sep. 29, 2015

(65) Prior Publication Data

US 2016/0095270 P1 Mar. 31, 2016

(30) Foreign Application Priority Data

Sep. 29, 2014 (AU) ..... PBR 2014/227

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Keith Robinson
(74) *Attorney, Agent, or Firm* — Samuel R. McCoy, Jr.

(57) ABSTRACT

'SAB01' is a new and distinct variety of *Rhagodia spinescens* which is characterized by the combination of a short plant height, shortened internodes, and a mounded and spreading growth habit. The new variety propagates successfully by stem cuttings and has shown to be uniform and stable in the resulting generations from asexual propagation.

3 Drawing Sheets

Latin name of genus and species: The Latin name of the genus and species of the novel variety disclosed herein is *Rhagodia spinescens*.

Variety denomination: The inventive variety of *Rhagodia spinescens* disclosed herein has been given the variety denomination 'SAB01'.

CROSS REFERENCE TO RELATED APPLICATIONS

This application claims priority to the Australian Plant Breeders Rights application number 2014/227, filed on Sep. 29, 2014, which is herein incorporated by reference.

BACKGROUND OF THE INVENTION

Parentage: 'SAB01' is a seedling selection which resulted from the open self-pollination of a single line of *Rhagodia spinescens* (not patented) at a commercial plant breeding facility in Clarendon, NSW, Australia. The objective of the selection process was to develop a very low-growing form of *Rhagodia spinescens*. In 2010, and again in 2011, seed was harvested from the species, *Rhagodia spinescens*, and germinated at a commercial plant breeding facility in Clarendon, NSW, Australia. The resulting seedlings were grown to a mature size in 140 mm nursery pots for evaluation. Those plants that exhibited a mounding habit and low plant height were isolated for further evaluation. In early 2012, three of said low-growing selections were planted into the landscape and allowed to fully mature. After a year of further evaluations, in the spring of 2013, it was determined that one of the three candidate plants maintained the desired low height and mounding habit. The selection was given the denomination, 'SAB01'.

Asexual Reproduction: 'SAB01' was first asexually propagated in the spring of 2013 by stem cuttings at a commercial plant breeding facility in Clarendon, NSW, Australia. 'SAB01' has since been successfully propagated through 5 successive generations. The distinctive characteristics of the inventive 'SAB01' variety are stable from generation to generation; plants of the variety produced by asexual reproduction maintain the distinguishing characteristics of the original plant.

SUMMARY OF THE INVENTION

The following characteristics have been repeatedly observed and represent the distinguishing characteristics of the new *Rhagodia spinescens* cultivar 'SAB01'. These traits, in combination, distinguish 'SAB01' as a new and distinct cultivar.

1. *Rhagodia spinescens* 'SAB01' exhibits a short plant height; and
2. *Rhagodia spinescens* 'SAB01' exhibits a rounded plant habit; and
3. *Rhagodia spinescens* 'SAB01' exhibits shortened internodes.

DETAILED BOTANICAL DESCRIPTION

Figure 1:
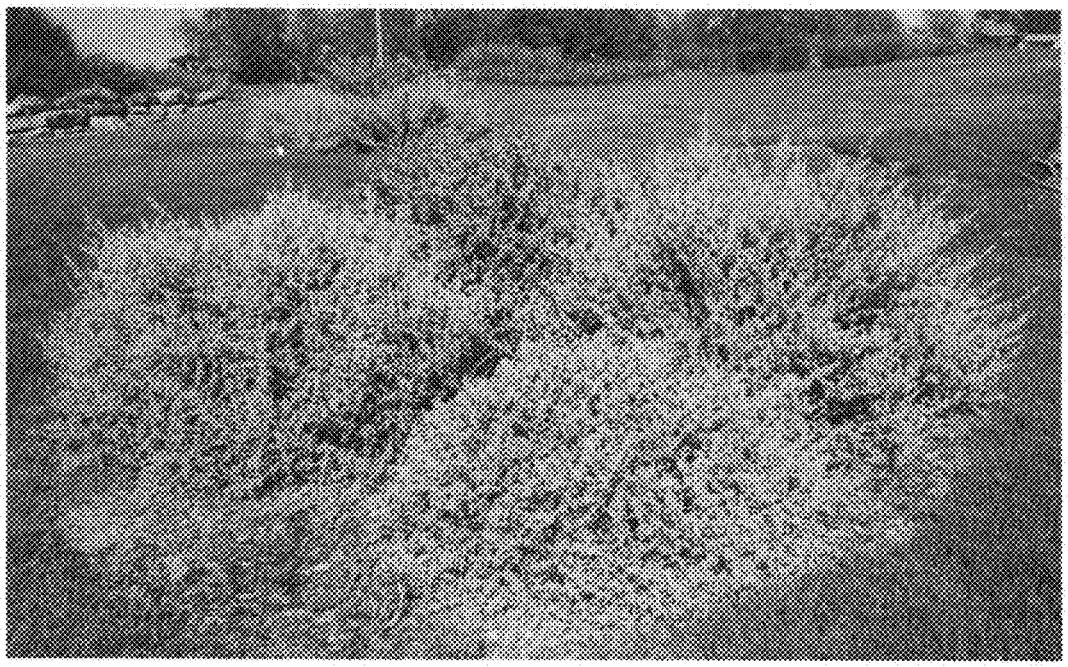
FIG. 1 illustrates as true as is reasonably possible to obtain in color photographs of this type, the original 'SAB01' plant (in the foreground of the photograph) at one and a half years of age. The original 'SAB01' plant is shown here with the two excluded candidate selections immediately behind the 'SAB01' plant, and also the parent plant in the rear. The low, mounding habit of 'SAB01' is easily discernable from the semi-upright habit of the excluded candidate selections and the parent plant.
Figure 2:
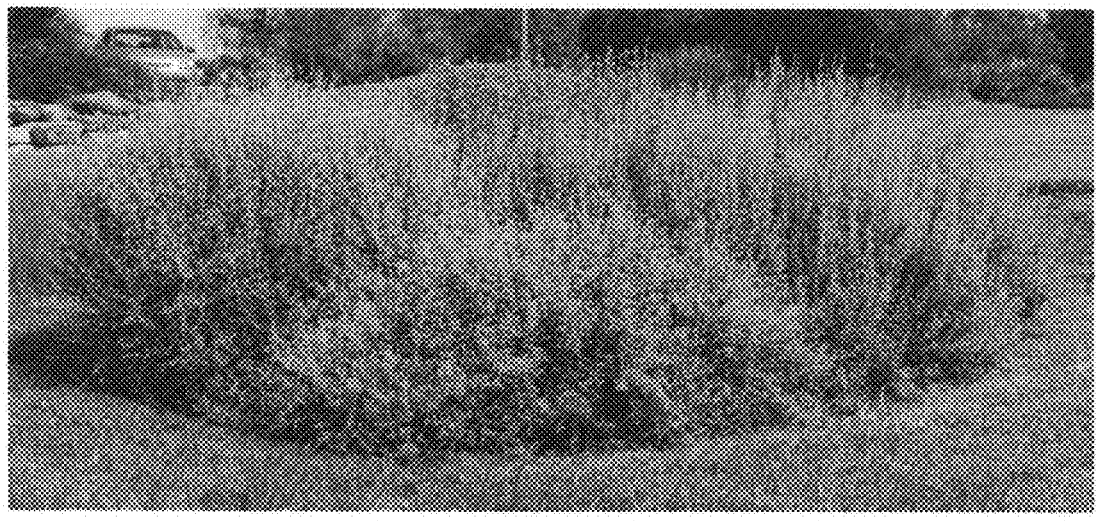
FIG. 2 illustrates as true as is reasonably possible to obtain in color photographs of this type, the same 'SAB01' plant of FIG. 1 (in the foreground of the photograph) at approximately three years of age. Said 'SAB01' plant is shown here with the two excluded candidate selections immediately behind the 'SAB01' plant, and also the parent plant in the rear. The low, mounding habit of 'SAB01' is easily discernable from the semi-upright habit of the excluded candidate selections and the parent plant.
Figure 3:
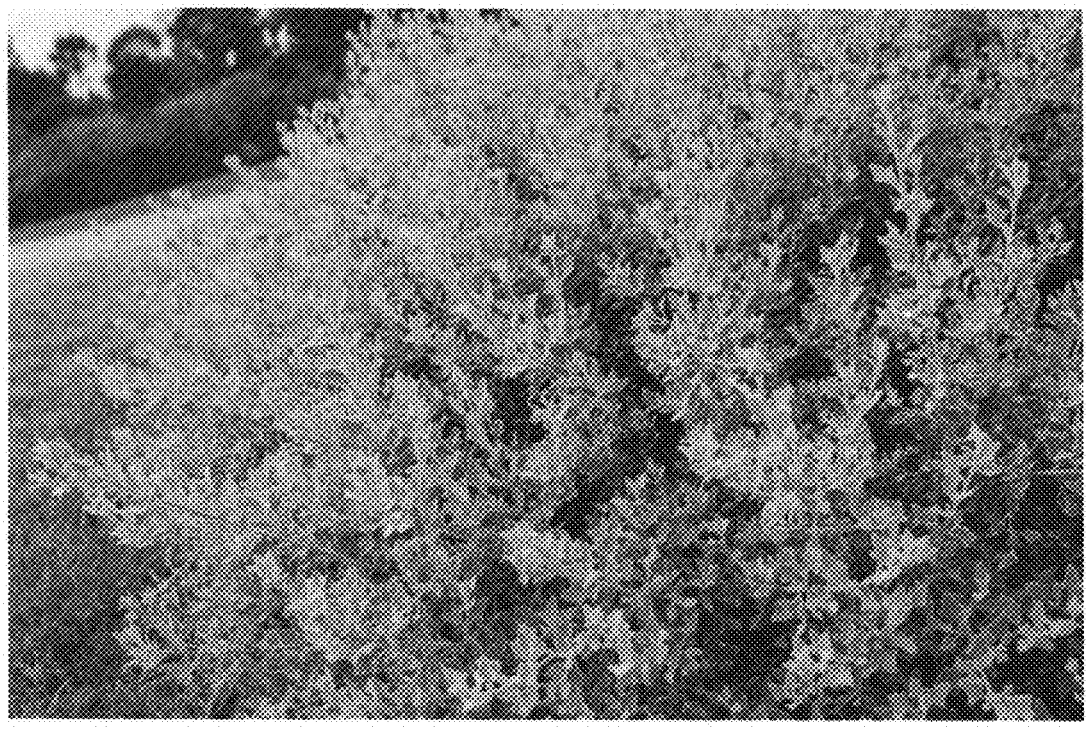
FIG. 3 illustrates as true as is reasonably possible to obtain in color photographs of this type, exemplary foliage of 'SAB01'.

The following is a detailed botanical description of a new and distinct variety of *Rhagodia spinescens* known as 'SAB01', based upon observations of 4 year old plants grown, in full sun in open landscape beds in Clarendon, New South Wales, Australia. Plants were maintained with granular slow release fertilizer and occasionally watered with overhead irrigation during periods of prolonged drought. No pest and disease measures were taken. Observation data was recorded in September of 2015.

Those skilled in the art will appreciate that certain characteristics will vary with older or, conversely, with younger plants. 'SAB01' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2001 edition except where common terms of color are used.

A botanical description of 'SAB01' and comparison with the parent are provided below.

General plant description:

*Growth habit*.—Mounded; spreading.
*Height*.—75 cm tall and 120 cm wide.
*Hardiness*.—USDA Hardiness Zones 9 to 11.
*Environmental tolerances*.—Tolerant of light frosts; highly salt and drought tolerant.
*Pests and diseases*.—No measures were taken.
*Propagation method*.—Softwood stem cuttings.
*Time to initiate roots*.—4 weeks.
*Time to produce a rooted cutting or liner*.—8 to 10 weeks.

Root system:

*Description*.—Tap root; orange-white (nearest to RHS 159D), fleshy roots.

Stems:

*Branching habit*.—Spreading; freely branching.
*Stem strength*.—Low; brittle.
*Dimensions*.—Immature stems are approximately 1.4 mm in diameter.
*Cross-section*.—Round.
*Internode length*.—7 mm.
*Color*.—191B.
*Texture and pubescence*.—Scabrous and pubescent.

Foliage:

*Arrangement*.—Opposite.
*Attachment*.—Petiolate.
*Shape*.—Ovate.
*Apex*.—Acute.
*Base*.—Attenuate.
*Dimensions*.—17 mm long and 6.5 mm wide.
*Leaf thickness*.—0.5 mm.
*Texture and pubescence, adaxial and abaxial surfaces*.—Scabrous and pubescent.
*Margin*.—Lobate.
*Juvenile color, adaxial and abaxial surfaces*.—199A.
*Mature color, adaxial surface*.—138B.
*Mature leaf color, abaxial surface*.—191B.
*Venation*.—Reticulate.
*Vein color* (*lower surface*).—138A.
*Vein color* (*upper surface*).—191B.

Inflorescence: Flowering has not been observed on the claimed plant.

Bud: Not observed.

Flower: Not observed.

Reproduction organs: Not observed.

Fruit and seed: Not observed.

COMPARISONS WITH THE PARENT

'SAB01' may be distinguished from its parent, *Rhagodia spinescens*, by the following combination of characteristics:

1. 'SAB01' has a short plant height of approximately 75 cm, whereas the parent has a medium plant height of approximately 100 to 125 cm.
2. 'SAB01' has a mounding and spreading growth habit, whereas the parent has a semi-erect growth habit.

COMPARISONS WITH THE MOST SIMILAR VARIETY OF COMMON KNOWLEDGE

'SAB01' may be distinguished from the most similar comparator, *Rhagodia spinescens* 'Silver Border' (not patented), by the following combination of characteristics:

1. 'SAB01' has a short plant height of approximately 75 cm, whereas 'Silver Border' has a tall plant height of approximately 125 to 200 cm.
2. 'SAB01' has a plant width of approximately 100 cm, whereas 'Silver Border' has a plant width of 200 to 300 cm.

That which is claimed is:

1. A new and distinct variety of plant named 'SAB01', as described and illustrated herein.

* * * * *